United States Patent [19]

Kikuchi et al.

[11] Patent Number: 5,837,248

[45] Date of Patent: Nov. 17, 1998

[54] PEPTIDE CAPABLE OF INDUCING IMMUNE RESPONSE TO HUMAN GASTRIC CANCER AND AGENT FOR PREVENTING OR TREATING HUMAN GASTRIC CANCER, CONTAINING THE PEPTIDE

[75] Inventors: Kokichi Kikuchi, No. 7-1, Fushimi 3-chome, Chuo-ku, Sapporo-shi, Hokkaido, Japan; Noriyuki Sato, Sapporo, Japan; Hiromitsu Sahara, Rishirifuji-machi, Japan; Takahiro Yasojima, Setana-gun, Japan; Yoshimasa Wada, Sapporo, Japan; Manabu Suzuki; Junji Hamuro, both of Kawasaki, Japan

[73] Assignees: Ajinomoto Co., Inc., Tokyo; Kokichi Kikuchi, Sapporo, both of Japan

[21] Appl. No.: 723,116

[22] Filed: Sep. 30, 1996

[30] Foreign Application Priority Data

Sep. 29, 1995 [JP] Japan .................................. 7-253491
Aug. 19, 1996 [JP] Japan .................................. 8-217140

[51] Int. Cl.⁶ .......................... A61K 38/08; A61K 39/00
[52] U.S. Cl. ..................... 424/185.1; 424/184.1; 424/193.1; 514/15; 514/16; 514/14; 530/328; 530/327
[58] Field of Search ............................. 424/184.1, 185.1, 424/193.1; 514/15, 16, 14; 530/328, 327

[56] References Cited

U.S. PATENT DOCUMENTS

| 4,478,823 | 10/1984 | Sanderson . |
|---|---|---|
| 4,738,927 | 4/1988 | Taniguchi et al. . |
| 5,399,669 | 3/1995 | Taniguchi et al. . |
| 5,468,481 | 11/1995 | Sharma . |
| 5,510,259 | 4/1996 | Sugamura et al. . |
| 5,550,214 | 8/1996 | Eberlein . |

OTHER PUBLICATIONS

Yasoshima et al. 1995 Cancer vol. 75 11489.

Abastado et al 1995 J. Exp. Med. 182:439.

Arimilli et al. 1996 Immunol. & Cell Biology 74:96.

Porgador et al, *J. Immunol.*, vol. 156, pp. 2918–2926 (1996).

Celluzzi et al, *J. Exp. Med.*, vol. 183, pp. 283–287 (1996).

Falk et al, *Immunogenetics*, vol. 40, pp. 238–241 (1994).

Noguchi et al, *Proc. Natl. Acad. Sci.*, vol. 92, pp. 2219–2223 (1995).

Elliott, *Advances in Immunol.*, vol. 65, pp. 47–109 (1996).

Aebischer et al, *Advances in Immunol.*, vol. 61, pp. 341–403 (1996).

Carbone et al, *J. Exp. Med.*, vol. 169, pp. 603–612 (1989).

*Primary Examiner*—Thomas M. Cunningham
*Assistant Examiner*—Martha Lubet
*Attorney, Agent, or Firm*—Oblon, Spivak, McClelland, Maier & Neustadt, P.C.

[57] ABSTRACT

A peptide that induces CTL against human gastric cancer cells is provided. A peptide having a specific amino-acid sequence and induces cytotoxic T cells that targets gastric cancer cells may be used as an agent for preventing or treating gastric cancer.

4 Claims, 4 Drawing Sheets

PEPTIDE CAPABLE OF INDUCING IMMUNE RESPONSE TO HUMAN GASTRIC CANCER AND AGENT FOR PREVENTING OR TREATING HUMAN GASTRIC CANCER, CONTAINING THE PEPTIDE

BACKGROUND OF THE INVENTION

1. Field of the Invention

The present invention relates to a peptide capable of inducing CTL (Cytotoxic T Lymphocytes; refer to Medical Immunology, revised 3rd edition, compiled by Kikuchi Kokichi) to human gastric cells in vivo or in vitro, and to a DNA encoding this peptide. More specifically, the present invention relates to a peptide capable of presenting CTL to human gastric cells by being bound to HLA-A31 antigen (Human Leucocyte Antigen; refer to Modern Immunology, 2nd edition, compiled by Yamamura Yuichi and Tada Tomio), and to a DNA encoding the peptide.

The present invention further relates to an agent useful for preventing or treating human gastric cancer, the agent containing a peptide capable of inducing CTL to a human gastric cancer cell in vivo or in vitro, and to a vaccine for preventing or treating human gastric cancer, the vaccine containing a recombinant virus or a recombinant bacterium having a DNA encoding such a peptide.

2. Discussion of the Background

For pharmacotherapy of malignant tumors, a chemotherapeutic agent which directly impairs tumor cells or an immunotherapeutic agent with which treatment is conducted by non-specifically activating an immunity of a host and enhancing a bioprotective function of the host has been used. However, there is currently no agent with which malignant tumors, above all, tumors of the digestive tract can completely be cured.

In recent years, researchers using tumors of animals, mainly mice, have revealed that tumors can completely be cured by enhancing an antigen-specific immune response to tumor-related antigens and tumor-specific antigens present in various tumor cells. Clinically, the treatment has been conducted by enhancing the antigen-specific immune response to these tumor-specific antigens.

With respect to agents or approaches by which tumors are treated upon enhancing the tumor antigen-specific immune response, it has been reported that a monoclonal antibody against an antigen which is expressed in tumor cells and mainly recognized by B cells is used, that a tumor-specific immune response is induced by administering to the patients their own tumor cells or solubilized fractions thereof which have been inactivated with radiation or medicines as a vaccine, and that in order to increase an immunogenicity of tumor cells, viruses or various cytokine genes are introduced into tumor cells and the thus-treated tumor cells are administered to the patients themselves, whereby a tumor-specific immune response is induced.

However, it is being made clear that T cells including CTL mainly act on tumor rejection in vivo. It has been currently clarified that the treatment using an antibody against a B-cell-recognition antigen is limited.

Further, it has been clarified that the immune response with the T cells acts either intensively or suppressively in a state where two functional sub-populations (Th1 and Th2 subsets) present in T cell populations are activated, and that the immune of tumor cells themselves containing plural antigens sometimes rather suppresses the immune response to the tumor cells.

Still further, with respect to the inoculation of inactivated tumor cells, the possibility of re-growth of tumors through re-activation in vivo cannot completely be denied. Thus, the problem of safety remains.

In order to sidestep the above-mentioned problems, a method is considered in which an antigen protein to activate CTL which is deemed to play a central role in tumor rejection is identified and CTL is activated using this antigen protein.

It has been clarified through advances of researches in recent years that CTL is induced such that a peptide which is fragmented by a protease in cells and which comprises from 8 to 12 antigen-protein-derived amino acids acts as an antigen presenting molecule to CTL by being bound to an HLA antigen.

Accordingly, regarding the cancer antigen peptide, it is considered that if a peptide which is bound to an HLA molecule to induce CTL to tumor cells can be discovered, this peptide can he used as an agent for preventing or treating cancers.

On the basis of these considerations, a cancer antigen peptide capable of inducing CTL has been studied. However, only a peptide derived from a protein, i.e. MAGE family, Mart-1, Tyrosinase, gp100, which is a cancer antigen present in melanoma tumors has been made clear to date. With respect to cancers of the digestive tract including gastric cancer, the presence of a cancer antigen peptide capable of inducing CTL and the structure of the cancer antigen peptide are currently unknown.

SUMMARY OF THE INVENTION

Accordingly, it is one object of the present invention to provide novel peptides capable of inducing an immune response to human gastric cancer.

It is another object of the present invention to provide novel DNA encoding such a peptide.

It is another object of the present invention to provide novel agents or compositions useful for treating or preventing human gastric cancer, which contain such a peptide.

It is another object of the present invention to provide novel recombinant viruses and novel recombinant bacteria which contain DNA encoding such a peptide.

If is another object of the present invention to provide novel vaccines useful for preventing human gastric cancer, which contain such a recombinant virus or recombinant bacterium containing DNA encoding such a peptide.

If is another object of the present invention to provide a novel method for preparing such a peptide by culturing such a recombinant virus or recombinant bacteria.

To achieve these objects, the present inventors have focused on the fact that CTL which recognizes the tumor antigen plays an important role as a bioprotective mechanism to tumor cells. That is, they have conducted studies in consideration of the fact that the efficient induction of CTL with a peptide which can be used as a part of a vaccine or with a transformant containing a DNA encoding the peptide is effective for preventing or treating cancers.

It has been known that the HLA antigen is bound to the cancer antigen peptide and acts as an antigen-presenting molecule to CTL whereby CTL is induced. Accordingly, it is considered that if a peptide which can activate CTL reactive with gastric cancer cells can be found, it is possible to use the same as an agent for preventing or treating the gastric cancer.

The present inventors have succeeded in establishing a CTL cell strain (Tc-HST-2) which is specifically reacted with gastric cancer cells restrained to HLA-A31, this strain being derived from the patient suffering from a gastric cancer, and they have succeeded in establishing a gastric cancer cell strain (HST-2) on which this CTL acts, this strain being derived from the same patient (*J. I. Meth.*, vol. 154, pp. 235–243 (1992) and *Cancer*, vol. 75, pp. 1484–1489 (1995)).

However, it has been unclear whether this CTL recognizes the tumor antigen and what antigen this CTL recognizes. On top of that, the presence of the cancer antigen peptide which exists specifically in cancers of the digestive tract including gastric cancer and which is capable of inducing CTL has not been clarified at all; much less has the essence thereof been clarified.

Accordingly, the present inventors have purified an HLA-bound peptide present on the cell surface of gastric cancer cell HST-2, and have identified a peptide that activates the CTL cell strain Tc-HST-2. Further, they have chemically synthesized this identified peptide in a conventional manner. Thus, it has been clarified for the first time that this peptide actually activates the CTL cell strain Tc-HST-2. Still further, it has been found that this peptide is expressed in gastric cancer cells other than HST-2.

From these results, it has been clarified that the above-mentioned peptide can be utilized well as an agent for preventing or treating gastric cancer. These findings have led to the completion of the present invention.

Thus, the present invention provides: (1) a peptide which is a fragment of a gastric cancer antigen protein present in a human gastric cancer cell, the fragment being bound to an HLA molecule and capable of inducing a cytotoxic T cell that targets the gastric cancer cell; (2) an agent for preventing or treating human gastric cancer, the agent containing the above-mentioned peptide; (3) a DNA encoding the above-mentioned peptide; and (4) a vaccine for preventing or treating human gastric cancer, the vaccine containing a recombinant virus or a recombinant bacterium having this DNA.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

The TNF-sensitive Wehi cells were impaired by the release of TNF, and incorporation of MTT by the residual cells is decreased. The peptide concentrations are 10 mM, 1 mM and 0.1 mM. In all of the tests, HST-2 was used as a target cell, and the ratio of target cells to CTL was 1:100.

Figure 6:
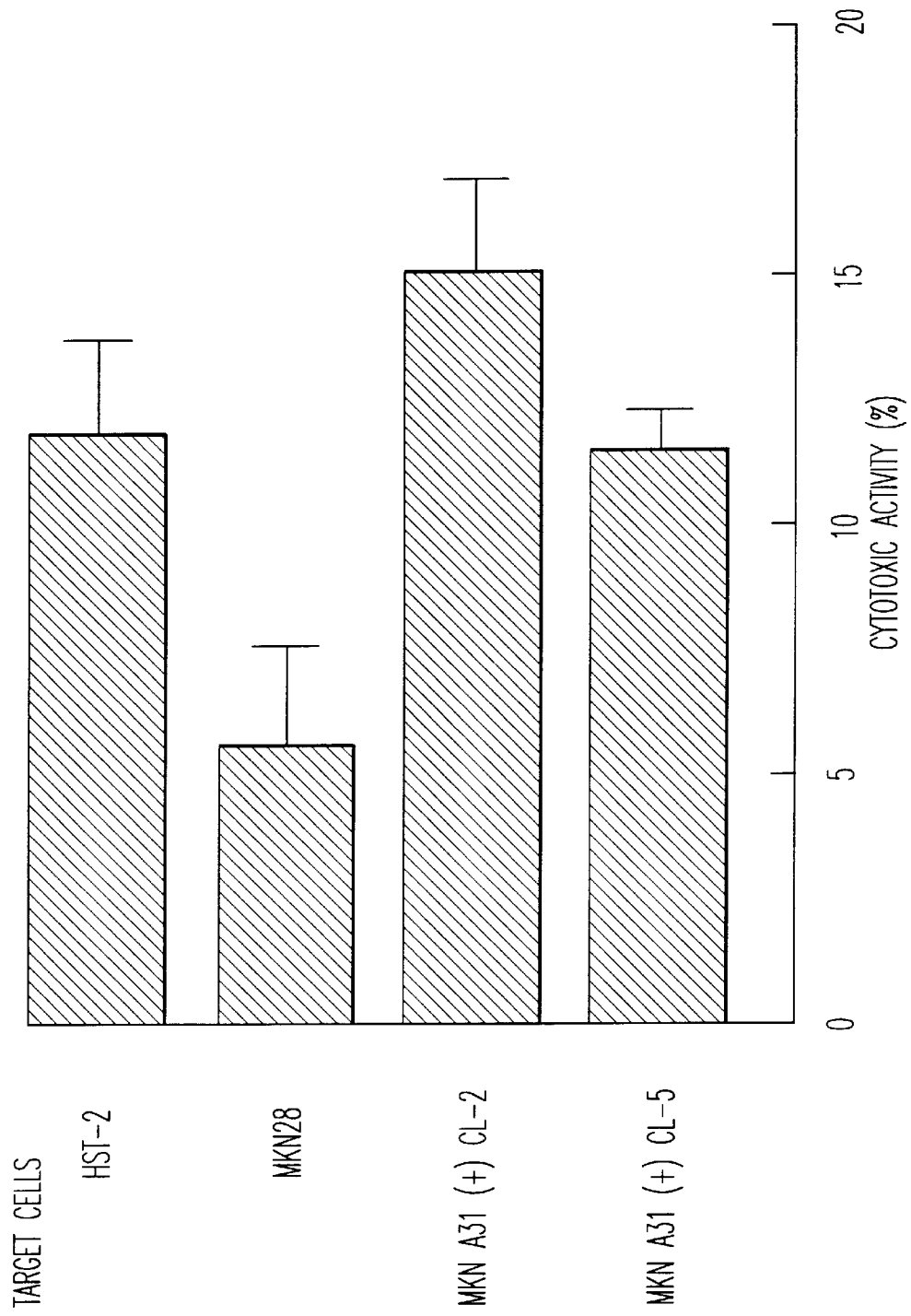

■ indicates the cytotoxicity when adding Peptide 1. □ indicates the cytotoxicity when adding Peptide 1-9. Δ indicates the cytotoxicity when adding Peptide 1-8. ○ indicates the cytotoxicity when adding Peptide 1-7. A broken line indicates a cytotoxicity when not adding a peptide; and FIG. 6 is a graph showing the cytotoxicity of TC-HST-2 when using MKN28 A31(+)cl-2 cells and MKN28 A31(+) cl-5 cells, which are sub-lines obtained by artificially expressing HLA-A31 and parental MKN28 gastric cancer cells. All of the tests were conducted such that the ratio of target cells to CTL was 1:100.

DESCRIPTION OF THE PREFERRED EMBODIMENTS

The present invention will be described in detail below.

In order to identify a peptide which is a fragment of a gastric cancer antigen protein present in a human gastric cancer cell, the fragment being bound to an HLA molecule and capable of inducing a cytotoxic T cell that targets the gastric cancer cell, it is indispensable to establish (1) a HLA-type human cancer cell strain that can be grown in vitro in a large amount and (2) a CTL cell strain which reacts with the above-mentioned cancer cell strain to restrain the HLA molecule and the T cell receptor, exhibiting a cytotoxicity and which can be grown in a large amount in vitro.

As an HLA-type human gastric cancer cell strain that can be grown in vitro in a large amount, for example, the HST-2 cell line established by the present inventors [*J. Immunol. Meth.*, vol. 154, pp. 235–243 (1992); and *Jpn. J. Cancer Res.*, vol. 84, pp. 906–913 (1993), which are incorporated herein by reference] can be used. This cell strain is a gastric signet ring cell carcinoma strain formed from carcinomatous ascites of a patient suffering from a gastric cancer.

Further, as a CTL cell strain which is reactive with the above-mentioned cancer cell strain to restrain the HLA molecule and the T cell receptor, exhibiting the cytotoxicity and which can be grown in a large amount in vitro, the Tc-HST-2 cell line established by the present inventors [*J. Immunol. Meth.*, vol. 154, pp. 235–243 (1992); and *Jpn. J. Cancer Res.*, vol. 84, pp. 906–913 (1993), which are incorporated herein by reference] can be used.

It is described in *Cancer*, vol. 75, pp. 1484–1489 (1995) that this CTL cell strain is specifically reactive with HST-2 cell and recognizes the HST-2 antigen and the HLA-A31 antigen at the same time.

HST-2 cells can be used to obtain the HLA-bound peptide containing the gastric cancer antigen peptide capable of inducing the CTL activity of the Tc-HST-2 cell strain. That is, the HST-2 cell is incubated under ordinary incubation conditions, for example, in an RPMI1640 medium containing fetal bovine serum. Then, the culture is washed with phosphate-buffer saline (PBS). Thereafter, an HLA molecule-bound peptide present on the cell surface is extracted efficiently with a 0.1% trifluoroacetic acid (TFA) solution. The extraction of the HLA-bound peptide using TFA is described in *Science*, vol. 249, pp. 283–287 (1990), which is incorporated herein by reference.

The gastric cancer antigen peptide capable of inducing the CTL activity of the Tc-HST-2 cell can be purified from the above-mentioned HLA-bound peptide through reversed-phase chromatography. The purification of this gastric cancer antigen peptide will be described later in the Examples in detail.

The Tc-HST-2-reactive gastric cancer antigen peptide in the HLA-bound peptide fraction which is separated through reversed-phase chromatography can be identified by measuring the CTL inducibility of each fraction in the same manner as described in *Science*, vol. 249, pp. 283–287 (1990), which is incorporated herein by reference.

That is, HLA-A31-positive HST-2 or KG-1 cells are radio-labeled with sodium chromate containing $^{51}$Cr, and are then mixed with the HLA-bound peptide separated through reversed phase chromatography. The mixture is incubated at 37° C. for 3 hours, and Tc-HST-2 is then added thereto. The resulting mixture is further incubated for 12 hours. The CTL inducibility can be detected by measuring the radioactivity of $^{51}$Cr released in the supernatant.

With respect to the gastric cancer antigen peptide capable of inducing the CTL activity of the Tc-HST-2 cell separated through the reversed-phase chromatography, the amino-acid sequence thereof can be determined in the usual manner using a solid-phase-technique protein sequencer. For example, a peptide represented by SEQ ID NO: 1 of the Sequence Listing can be mentioned as a peptide exhibiting the CTL inducibility.

Needless-to-say, the peptide having the amino-acid sequence represented by SEQ ID NO: 1 of the Sequence Listing can be used in the present invention. Further, a peptide having an amino-acid sequence obtained by modifying a part of the amino-acid sequence represented by SEQ ID NO: 1 of the Sequence Listing can also be used, this fragment being bound to an HLA molecule and capable of inducing a cytotoxic T cell that targets a gastric cancer cell.

Specific examples of a peptide having an amino-acid sequence obtained by modifying a part of the amino-acid sequence represented by SEQ ID NO: 1 of the Sequence Listing in the present invention include (1) an amino-acid sequence obtained by replacing at least one amino acid in the amino-acid sequence represented by SEQ ID NO: 1 of the Sequence Listing with another amino acid; (2) an amino-acid sequence obtained by deleting at least one amino acid from the N-terminus or C-terminus of the peptide having the amino-acid sequence represented by SEQ ID NO: 1 of the Sequence Listing; and (3) a peptide which contains the amino-acid sequence represented by SEQ ID NO: 1 of the Sequence Listing as a part of the overall amino-acid sequence.

The peptide of the present invention ranges from a peptide formed by binding a few amino acids to a peptide formed by binding many amino acids.

Even a peptide having an amino-acid sequence obtained by modifying a part of the amino-acid sequence represented by SEQ ID NO: 1 of the Sequence Listing cannot be used in the present invention unless it is capable of inducing a cytotoxic T cell that targets a gastric cancer cell.

For example, the peptide having the amino-acid sequence represented by SEQ ID NO: 2 of the Sequence Listing can be used in the present invention, but the peptides having the amino-acid sequences represented by SEQ ID NO: 3 and SEQ ID NO: 4 of the Sequence Listing cannot be used, because they exhibit no CTL inducibility (refer to Example which will be later described).

The method of producing the above-mentioned peptide is not particularly limited. The peptide may be produced using a solid-phase peptide synthesis technique or a recombinant DNA technique.

Specifically, a CTL-inducible peptide that targets a gastric cancer cell as represented by SEQ ID NO: 1 or SEQ ID NO: 2 of the Sequence Listing may be synthesized using the usual solid-phase peptide synthesis technique. It may also be produced by incorporating a DNA encoding amino acids constituting this peptide into an appropriate expression vector, and incubating the thus-transformed BCG bacteria or bacteria belonging to the genus *Escherichia coli*.

The DNA encoding the peptide having the amino-acid sequence represented by SEQ ID NO: 1 or SEQ ID NO: 2 of the Sequence Listing can be deduced from the amino-acid sequence. Codons corresponding to each amino acid sequence are naturally well known to those skilled in the art.

All of the peptides of the present invention were purified by reversed-phase HPLC, and it was confirmed through reversed-phase HPLC that these are single components. Then, the peptides were identified through mass analysis, and were used in CTL assay.

The peptides of the present invention can induce the CTL activity to the gastric cell-specific CTL strain, Tc-HST-2. The CTL inducibility can be measured by the above-mentioned Cr-releasing method or by the TNF-releasing method described in *Immunogenetics*, vol. 35, p. 145 (1992), which is incorporated herein by reference.

That is, in the TNF-releasing method, the HLA-A31-positive HST-2 or KG-1 cell is mixed with the peptide of the present invention, and the mixture is incubated at 37° C. for 3 hours. Then, Tc-HST-2 cells are added thereto, and the resulting mixture is further incubated for 12 hours. The activity of any TNF released in the supernatant is measured to detect the CTL inducibility.

The TNF activity can be measured by the method described in *Immunogenetics*, vol. 35, p. 145 (1992).

That is, TNF-sensitive Wehil64 cells are mixed with a test sample, and the mixture is incubated for 24 hours. Then, an MTT [3-(4,5-dimethylthiazol-2-yl)-2,5-diphenyl tetrazolium bromide] solution is added to the culture, and the resulting mixture is further incubated for 3 hours. After any formazan converted within mitochondria is dissolved in acid propanol, the amount thereof is measured in terms of an absorbance at OD570 to detect the TNF activity.

The peptides of the present invention, for example, the peptide having the amino-acid sequence represented by SEQ ID NO: 1 of the Sequence Listing can induce gastric cancer cell-specific CTL as a T cell epitope. Accordingly, it is expected to be effective as an agent for preventing or treating human gastric cancer.

In actual use, the peptides of the present invention can be administered: (1) as such; (2) along with a pharmaceutically acceptable carrier and/or diluent; or (3) further along with the following adjuvants as required, using a syringe or through subcutaneous absorption from a mucous membrane by spraying or the like. The carrier may be a human serum albumin or the like, and the diluent may be PBS, distilled water, or the like.

In the present invention, the agent for preventing or curing the human gastric cancer contains from 0.01 to 100% by weight, preferably from 0.1 to 95% by weight of a peptide which is a fragment of a gastric cancer antigen protein present in a human gastric cancer cell, the fragment being bound to an HLA molecule, specifically, an HLA-A31 molecule, and capable of inducing a cytotoxic T cell that targets the gastric cancer cell.

This agent is administered to an adult person at such a dose that the amount of the peptide of the present invention is between 0.01 mg and 100 mg in one administration. However, this range is only a standard, and it is not critical.

The formulation of the preparation is not particularly limited. A freeze-dried agent or a granular agent containing a vehicle such as saccharide may also be used.

This preparation has no problematic acute toxicity in the above-mentioned administration.

The adjuvants which may be added to the agent of the present invention to increase the CTL inducibility include microorganisms such as BCG, ISCOM described in *Nature*, vol. 344, p. 873 (1990), which is incorporated herein by reference, saponin-type QS-21 described in *J. Immunol.*, vol. 148, p. 1438 (1992), which is incorporated herein by reference, liposomes and aluminum hydroxide.

Further, an immunological activator can be used as an adjuvant. Examples thereof include lentinan, schizophyllan and picibanil. Cytokines that enhance growth or differentiation of T cells, such as IL-2, IL-4, IL-12, IL-1, IL-6 and TNF can also be used as adjuvants.

It is described in the above-mentioned literature and in *Science*, vol. 255, p. 333 (1992), which is incorporated herein by reference, that the immune response of CTL or the like can be induced in vivo by the above-mentioned method.

Further, it is possible that the above-mentioned antigen peptide may be added in vitro to cells collected from a patient or cells having the same HLA haplotype in order to present the antigen, after which these cells are administered to the blood vessel of the patient to effectively induce CTL within the body of the patient. Still further, it is possible that the above-mentioned peptide may be added to peripheral blood lymphocytes of the patient and the peptide-containing lymphocytes are incubated in vitro to induce CTL in vitro, after which the resulting lymphocytes are returned to the blood vessel of the patient. The treatment through such a cell transfer has been already practiced as a cancer therapy, and it is well known to those skilled in the art.

The DNA encoding the gastric cancer antigen peptides of the present invention is inserted into an appropriate vector; viruses such as vaccinia virus or bacteria such as BCG, which contain this recombinant DNA, can effectively be used as a live vaccine for preventing or treating human gastric cancer.

That is, when: (1) a DNA encoding the peptide having the amino-acid sequence represented by SEQ ID NO: 1 of the Sequence Listing or (2) a DNA encoding a peptide having the amino-acid sequence obtained by modifying a part of the amino-acid sequence represented by SEQ ID NO: 1 of the Sequence Listing (for example, a peptide having an amino-acid sequence represented by SEQ ID NO: 2 of the Sequence Listing) is inserted into an antigen protein gene which is expressed in the recombinant viruses or the recombinant bacteria, this peptide sequence is expressed as a part of the antigen protein, then processed in the cells, and presented to the HLA antigen, making it possible to induce CTL that recognizes the same.

The dose and the administration method of the agent are the same as those in usual vaccination or administration of BCG vaccine.

Other features of the invention will become apparent in the course of the following descriptions of exemplary embodiments which are given for illustration of the invention and are not intended to be limiting thereof.

EXAMPLES

Example 1

Purification of Tc-HST-2 response peptide from HST-2 and identification thereof:

HST-2 cells (2×105 cells/ml) were inoculated in 50 ml of a 10% FCS-containing RPMI1640 medium (containing 2 mM glutamine, $5 \times 10^{-5}$ M 2ME, 100 units/ml of penicillin, 100 μg/ml of streptomycin and 16 mM $NaHCO_3$) in a 175 $cm^2$ plastic incubator (cat. No. 3028, manufactured by Falcon), and were incubated in the presence of a 5% $CO_2$ gas in air at 37° C. for 4 days.

After the completion of the incubation, the supernatant formed was removed, and the residue was washed with PBS (-). Then, 20 ml of 0.1% TFA solution were added thereto, and the mixture was incubated at 4° C. for 30 minutes. An HLA-bound peptide was released from the HLA molecule. The HLA-bound peptide released was centrifuged at 10,000 g for 15 minutes to separate the cell residue therefrom.

Twenty milliliters of the HLA-bound peptide solution obtained by incubating HST-2 as mentioned above were freeze-dried and dissolved in 5 ml of a 0.1% TFA solution. One milliliter of this HLA-bound peptide solution was treated with a reversed-phase HPLC column (μ BONDSHERE, 5 μ C18-300 A, 19 mm×150 mm). The reversed-phase HPLC column had been equilibrated with 0.1% TFA-containing distilled water in advance, and then the targeted substance was eluted by increasing the concentration of acetonitrile in 0.1% TFA linearly from 0 to 80%. This procedure was conducted at a flow rate of 1 ml/min. The eluent was collected in amounts of 1 ml each.

Figure 1:
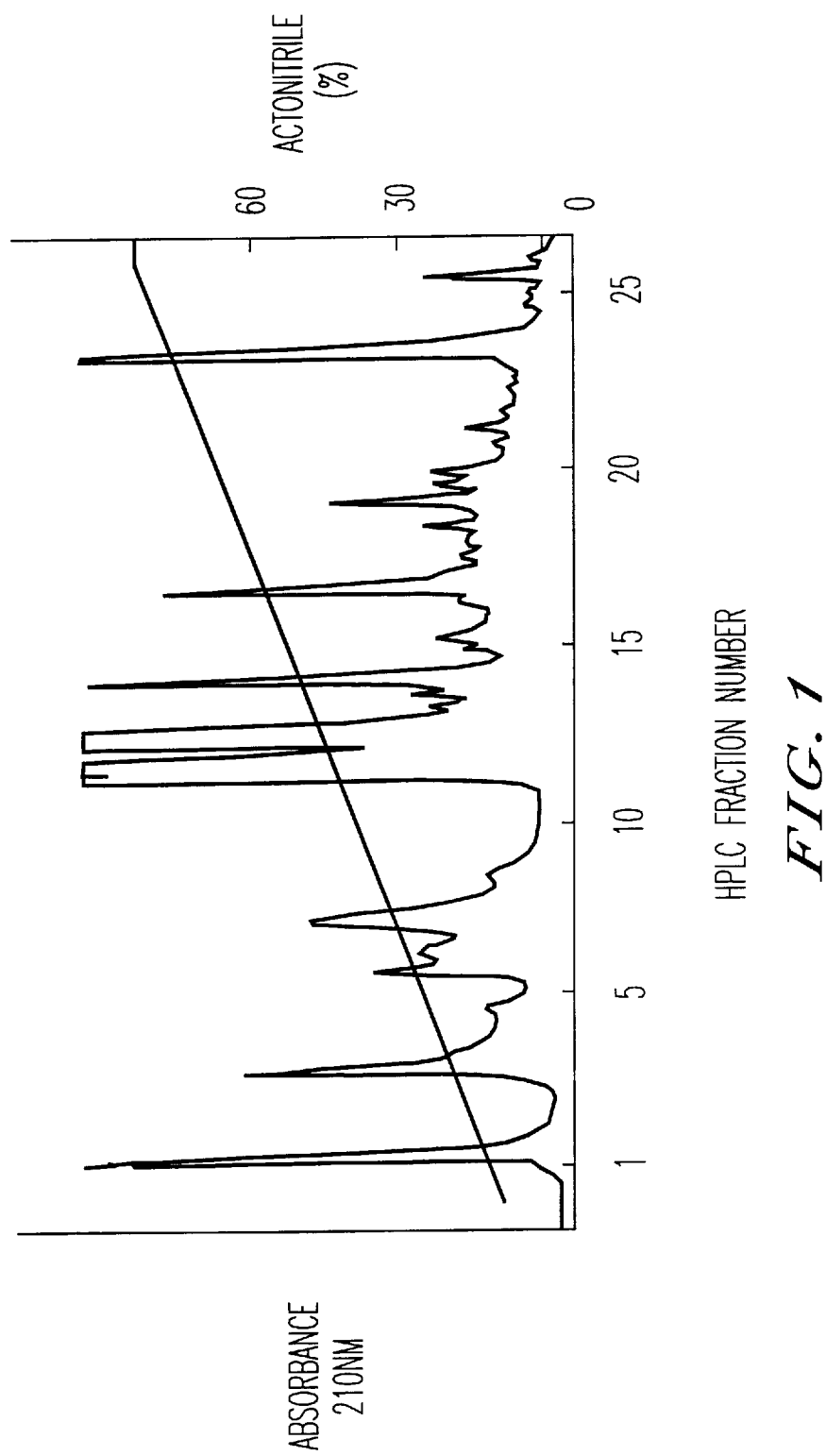
FIG. 1 is an elution pattern of an HLA-bound peptide from HST-2 gastric cancer cells in a reversed-phase HPLC column. The line indicates the acetonitrile concentration, and the curve indicates the absorbance at OD210 in each concentration.

The above procedure was repeated for a total of 10 times. Fractions that showed the same retention time were collected, and freeze-dried. No significant difference was found in elution patters of HPLC in the above-mentioned procedures. The elution patterns of HPLC are shown in FIG. 1.

The CTL inducibility of the HPLC elution fractions against Tc-HST-2 cells was measured as follows. That is, $1 \times 10^6$ HST-2 or KG-1 cells expressing HLA-A31 antigen as target cells were suspended in a 10% FCS-containing RPIM medium such that the number of cells reached $1 \times 10^7$ cells/ml. To the suspension were added 100 μl of a mixture of sodium chromate containing $^{51}Cr$ and PBS, and the resulting mixture was incubated in the presence of 5% $CO_2$ at 37° C. for 3 hours for $^{51}Cr$-labeling. The $^{51}Cr$-labeled cells ($1 \times 10^4$ cells) were suspended in 100 μl of the solution. Three microliters of the solution containing the HLA-bound peptide separated through HPLC were added thereto, and the mixture was further incubated under the same conditions for 3 hours, whereby the HLA-bound peptide was bound to the HLA molecule.

Subsequently, Tc-HST-2 cells (2.5×105 cells/ml) were added thereto in an amount of 100 μl, and the mixture was incubated under the same conditions for 12 hours. After 12 hours of incubation, 100 μl of the supernatant formed were collected, and the radioactivity of $^{51}Cr$ released in this supernatant was measured using a γ-counter to measure the CTL activity.

The specific cytotoxicity was calculated using the following formula.

$$\text{Specific Cytotoxcity} = \frac{(\text{measured value of each well}) - (\text{minimum release value})}{(\text{maximum release value}) - (\text{minimum release value})} \times 100$$

wherein the minimum release value indicates a measured value of a well filled with target cells alone and a value of $^{51}$Cr naturally released from target cells, and the maximum release value indicates a release value when the cells are destroyed by adding a surfactant, 1% Triton x-100, to target cells.

Figure 2:
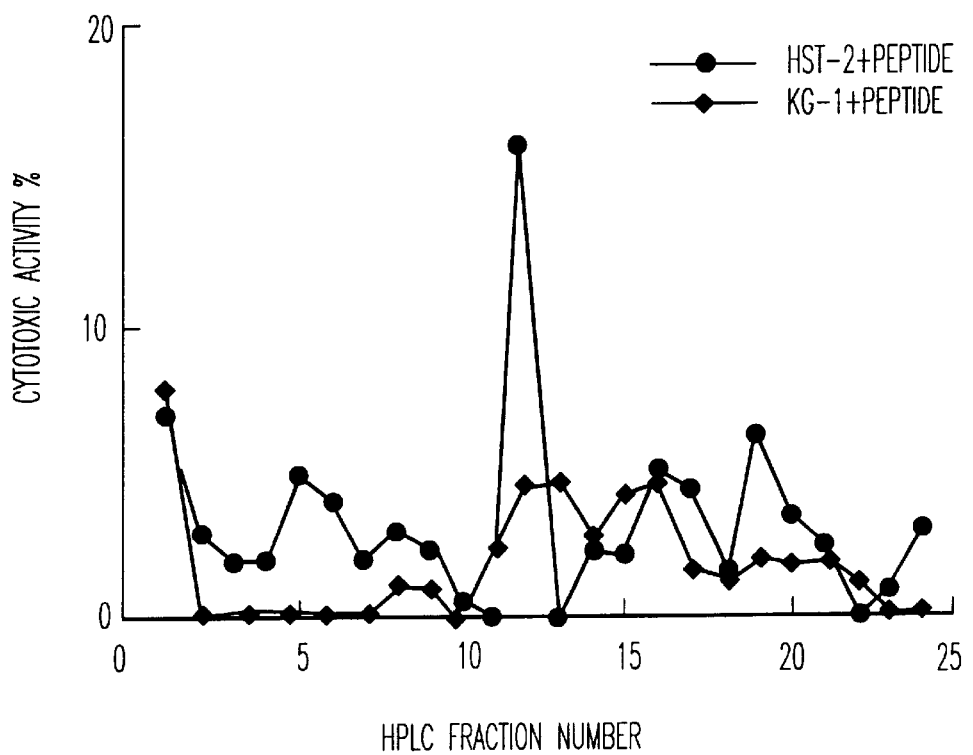
FIG. 2 is a graph showing the specific cytotoxicity of Tc-HST-2 when using an HST-2-derived HLA-bound peptide. ○ indicates the specific cytotoxicity when using HST-2. ♦ indicates the cytotoxicity when using an HLA-A31-positive KG-1 cell as a target cell. All of the tests were conducted such that the ratio of target cells to CTL was 1:100.

The results are shown in FIG. 2. As is made clear from FIG. 2, the CTL inducibility was observed in the 12th fraction eluted through HPLC.

The 12th fraction of which the CTL inducibility of Tc-HST-2 had been identified was further treated with a reversed-phase HPLC column ($\mu$ BONDSHERE, 5 $\mu$C18-300A, 19 mm×150 mm). The reversed-phase HPLC column had been equilibrated with 0.1% TFA-containing distilled water in advance, and then the targeted substance was eluted by increasing the concentration of acetonitrile in 0.1% TFA-containing eluent linearly from 0 to 40%. This procedure was conducted at a flow rate of 1 ml/min. The eluent was collected in amounts of 1 ml each.

Figure 3:
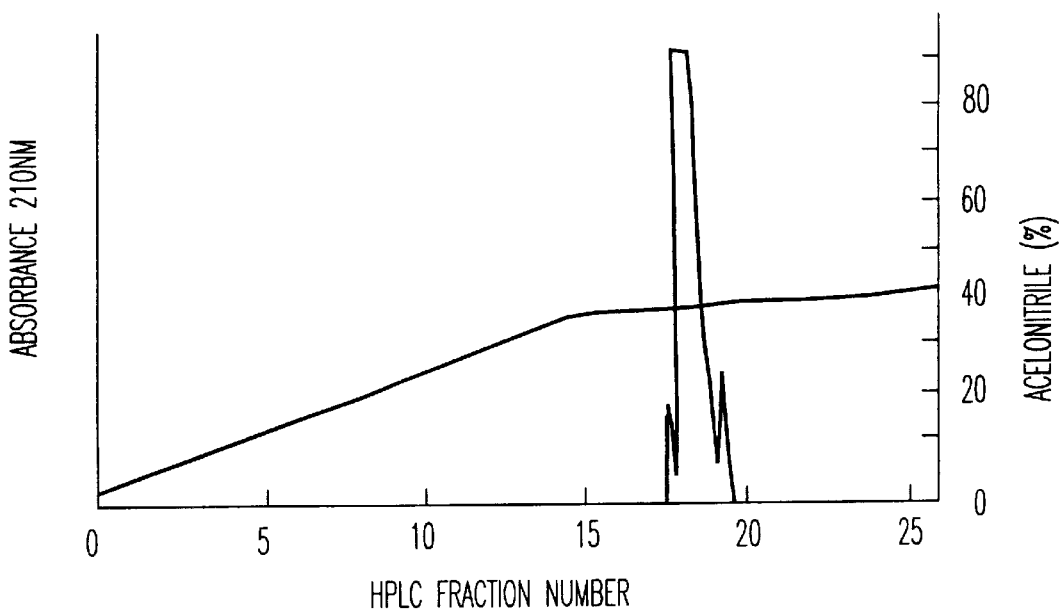
FIG. 3 is a elution pattern of a 12th fraction showing a CTL inducibility shown in FIG. 2 by a reversed-phase HPLC column. The line indicates the acetonitrile concentration, and the curve indicates the absorbance at OD210 in each concentration.

The above-described procedure was repeated for a total of 10 times. Fractions that showed the same retention time were collected and freeze-dried. No significant difference was found in elution patterns of HPLC in the above-mentioned procedures. The elution patterns of HPLC are shown in FIG. 3.

Figure 4:
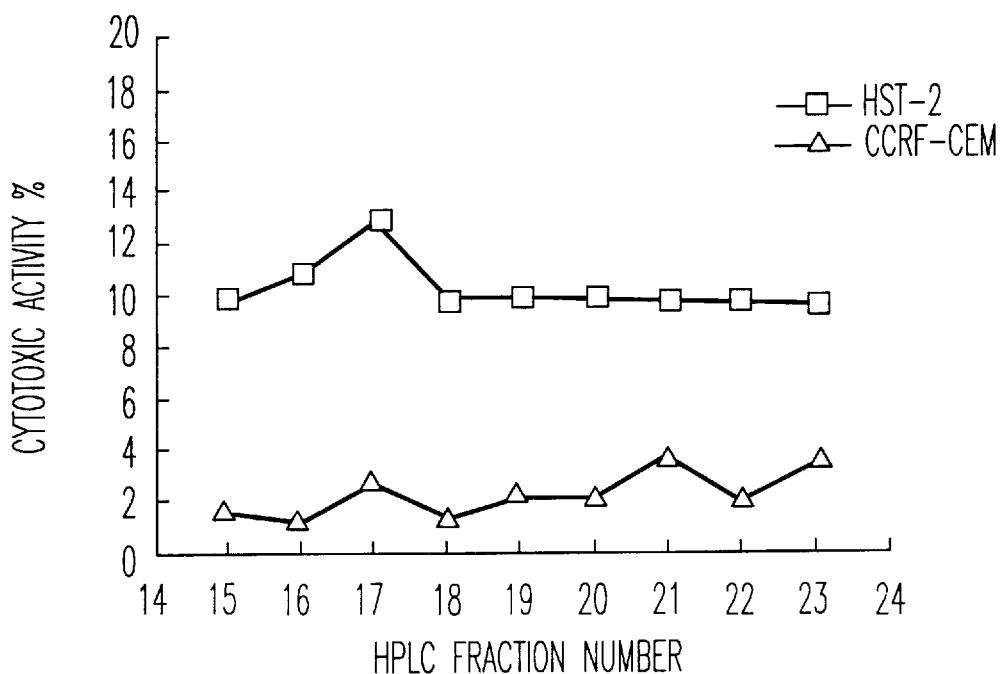
FIG. 4 is a graph showing the specific cytotoxicity of Tc-HST-2 when using an HST-2-derived HLA-bound peptide. □ indicates the specific cytotoxicity when using HST-2 as the target cell. ♦ indicates the cytotoxicity when using an HLA-A31-positive CCRF-CEM cell as the target cell. All of the tests were conducted such that the ratio of target cells to CTL was 1:100.

The CTL inducibility of Tc-HST-2 cells in the HPLC elution fractions was measured by the above-mentioned method. The results are shown in FIG. 4. As is made clear from FIG. 4, the CTL inducibility was identified in the 17th fraction eluted through HPLC.

The 17th fraction of which the CTL inducibility had been identified was separated with a reversed-phase HPLC column for analysis (ZORBAX, ODS column, 4 mm×250 mm). The reversed-phase HPLC column had been equilibrated with 0.1% TFA-containing distilled water in advance, and then the targeted substance was eluted by increasing the concentration of acetonitrile in 0.1% TFA-containing elution linearly from 0 to 60%. This procedure was conducted at a flow rate of 1 ml/min to obtain a main peak.

This peak was separated and introduced into a protein sequencer (477A, manufactured by ABI). The amino-acid sequence was determined by the Edman degradation method. The amino-acid sequence from the N-terminus is represented by SEQ ID NO: 1 of the Sequence Listing.

Example 2

Synthesis of a gastric cancer antigen peptide and measurement of CTL inducibility:

Synthetic Peptide 1 having the same amino-acid sequence as that represented by SEQ ID NO: 1 of the Sequence Listing and three types of peptides containing from 9 to 7 amino acids starting from the N-terminus of this Synthetic Peptide 1, namely: Peptide 1-9 (the peptide having the amino-acid sequence represented by SEQ ID NO: 2 of the Sequence Listing); Peptide 1-8 (the peptide having the amino-acid sequence represented by SEQ ID NO: 3 of the Sequence Listing); and Peptide 1-7 (the peptide having the amino-acid sequence represented by SEQ ID NO: 4 of the Sequence Listing) were synthesized using an automated peptide synthesizer (477A, manufactured by ABI) according to a protocol in the manual of the same machine.

These synthetic peptides were cut from the resin, and re-precipitated with a mixture of TFA and dry ether. They were identified to be single components through reversed phase HPLC, and were further identified using a mass spectrometer. Subsequently, they were subjected to CTL assay using a TNF-releasing method.

That is, 1×10$^4$ HST-2 cells expressing HLA-A31 antigen were suspended as target cells in 100 $\mu$l of the solution, and 5 $\mu$l of each of the above-mentioned four synthetic peptides were added thereto such that the final concentration reached 10 $\mu$M, 1 $\mu$M or 0.1 $\mu$M. The mixture was further incubated under the same conditions for 3 hours to bind the HLA-bound peptide to the HLA molecule. Subsequently, Tc-HST-2 cells (1×10$^6$ cells/ml) were added thereto in an amount of 100 $\mu$l, and the resulting mixture was further incubated for 12 hours under the same conditions.

After 12 hours of incubation, 30 $\mu$l of the supernatant formed was collected, and the TNF activity released in the supernatant was measured to detect the CTL inducibility. The TNF activity was measured by the following method.

That is, 7×10$^4$ Wehil64 cells which are TNF-sensitive cells were suspended in 120 $\mu$l of the solution, and 30 $\mu$l of the above-obtained supernatant were added thereto. The mixture was incubated for 24 hours. After the completion of the incubation, 5 mg/ml of MTT were added to each well in amounts of 10 $\mu$l each, and the mixture was further incubated for 3 hours. Subsequently, 150 $\mu$ of propanol containing 0.01% hydrochloric acid were added thereto to solubilize any formazan formed during the incubation. Then, the absorbance was measured at a wavelength of 570 nm to measure the TNF activity.

Figure 5:
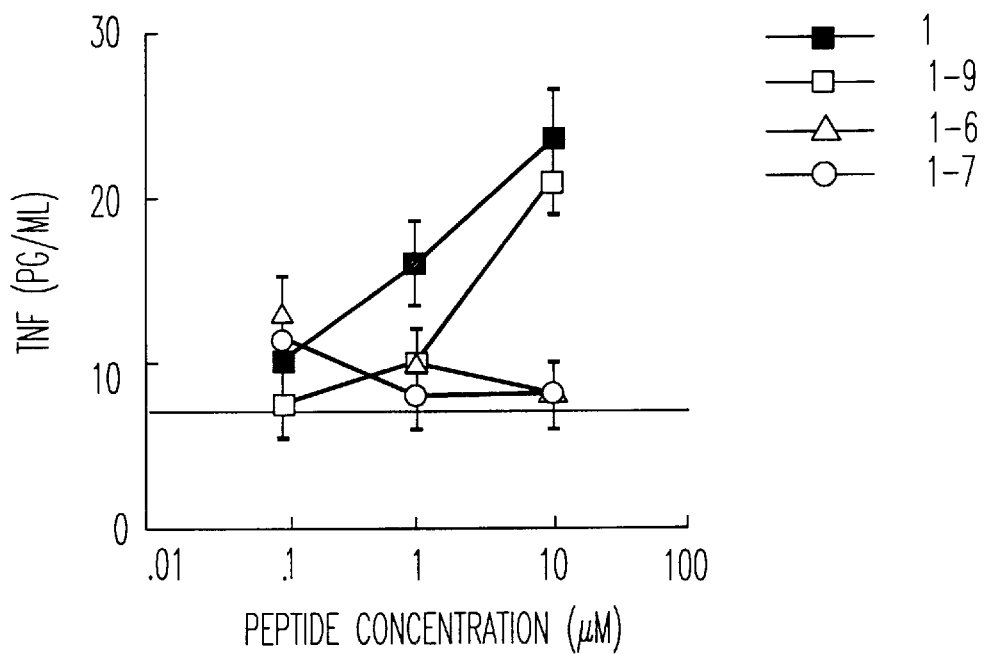
FIG. 5 is a graph showing the CTL inducibility of Tc-HST-2 measured by the TNF-releasing method when using Peptide 1 (the peptide represented by SEQ ID NO: 1 of the Sequence Listing); Peptide 1-9 (the peptide represented by SEQ ID NO: 2 of the Sequence Listing); Peptide 1-8 (the peptide represented by SEQ ID NO: 3 of the Sequence Listing); and Peptide 1-7 (the peptide represented by SEQ ID NO: 4 of the Sequence Listing).

The results are shown in FIG. 5. As is made clear from FIG. 5, the CTL inducibility of TC-HST-2 was identified in Synthetic Peptides 1 and 1-9.

Example 3

Expression of a gastric cancer antigen peptide in the human MKN28 gastric cancer cell strain:

In order to identify whether or not a gastric cancer antigen peptide recognized by TC-HST-2 was expressed in gastric cancer cell strains other than HST-2, the cytotoxicity given by TC-HST-2 to MKN28 which is an HLA-A31-negative human gastric cancer cell strain was detected by the $^{51}$Cr-releasing method. The detection of the CTL activity by the $^{51}$Cr-releasing method was conducted in the same manner as in Example 1. The results are shown in FIG. 6. TC-HST-2 did not exhibit a cytotoxicity to the MKN28 cells which did not express HLA-A31. On the other hand, TC-HST-2 exhibited a significant cytotoxicity to MKN28 A31(+)cl-2 and MKN28 A31(+)cl-5, sub-lines of MNK28 formed by transfecting the plasmid pBJ-A31 containing the HLA-A31 gene into MKN28 through electroporation to express HLA-A31, as shown in FIG. 6.

From the above-mentioned results, it was identified that the gastric cancer antigen peptide recognized by TC-HST-2 was also expressed in MKN28, and that this peptide was bound to the HLA-A31 molecule and recognized by TC-HST-2.

The peptide of the present invention can induce CTL against human gastric cancer cells in vivo or in vitro, and this peptide itself and an agent comprising this peptide can be expected to act as an agent for preventing or treating human gastric cancer. Further, a recombinant virus or a recombinant bacterium containing DNA encoding the peptide capable of inducing CTL against human gastric cancer cells in vivo or in vitro exhibits quite a satisfactory pharmaceutical effect as a vaccine for preventing or treating human gastric cancer.

The present application is based on Japanese Patent Application Nos. 253491/1995 and 217140/1996, filed on Sep. 29, 1995, and Aug. 19, 1996, respectively, both of which are incorporated herein by reference in their entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A peptide which is a fragment of a gastric cancer antigen protein present in a human gastric cancer cell wherein said peptide comprises SEQ. ID. NO. 1 and consists of 10–12 amino acid residues and wherein said peptide is capable of binding to HLA-A3 1 and is capable of inducing a cytotoxic T cell that targets said gastric cancer cell.

2. A peptide which is a fragment of a gastric cancer antigen protein present in a human gastric cancer cell wherein said peptide comprises SEQ. ID. NO. 2 and consists of 9–12 amino acid residues and wherein said peptide is capable of binding to HLA-A31 and is capable of inducing a cytotoxic T cell that targets said gastric cancer cell.

3. A composition which is prepared by incubating a peptide of claim 1 or 2 with an HLA-A31 molecule in conditions suitable to form a complex wherein said complex is capable of inducing a cytotoxic T cell that targets said gastric cancer cell.

4. A method of reducing the severity of gastric cancer comprising administering to a patient in need thereof an effective amount of composition of claim 3.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN ( x i ) SEQUENCE DESCRIPTION: SEQ ID NO:1:

Tyr  Ser  Trp  Met  Asp  Ile  Ser  Cys  Trp  Ile
    1                  5                            10

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN ( x i ) SEQUENCE DESCRIPTION: SEQ ID NO:2:

Tyr  Ser  Trp  Met  Asp  Ile  Ser  Cys  Trp
    1                  5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN ( x i ) SEQUENCE DESCRIPTION: SEQ ID NO:3:

Tyr  Ser  Trp  Met  Asp  Ile  Ser  Cys
    1                  5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single -continued (D) TOPOLOGY: linear (i i) MOLECULE TYPE: peptide (v i) ORIGINAL SOURCE:
  (A) ORGANISM: HUMAN (x i) SEQUENCE DESCRIPTION: SEQ ID NO:4:

Tyr Ser Trp Met Asp Ile Ser
1               5